United States Patent [19]

Bevilacqua

[11] Patent Number: 5,509,907
[45] Date of Patent: Apr. 23, 1996

[54] SYRINGE NEEDLE GUARD ASSEMBLY

[75] Inventor: Al Bevilacqua, Naperville, Ill.

[73] Assignee: Med-Safe Products, Inc., New Lenox, Ill.

[21] Appl. No.: 405,724

[22] Filed: Mar. 17, 1996

[51] Int. Cl.$^6$ ............................................. A61M 5/32
[52] U.S. Cl. ........................................ 604/263; 604/192
[58] Field of Search .............................. 604/192, 187, 604/263, 110, 198

[56] References Cited

U.S. PATENT DOCUMENTS

| | | | |
|---|---|---|---|
| 4,664,259 | 5/1987 | Landis | 206/365 |
| 4,909,792 | 3/1990 | Norelli | 604/192 |
| 4,976,699 | 12/1990 | Gold | 604/192 |
| 4,982,842 | 1/1991 | Hollister . | |
| 5,017,189 | 5/1991 | Boumendil | 604/192 |
| 5,055,102 | 10/1991 | Stitnik | 604/192 |
| 5,116,325 | 5/1992 | Paterson | 604/192 |
| 5,135,509 | 8/1992 | Olliffe | 604/192 |
| 5,147,319 | 9/1992 | Ishikawa et al. | 604/174 |
| 5,151,089 | 9/1992 | Kirk, III et al. | 604/192 |
| 5,188,611 | 2/1993 | Orgain | 604/192 |
| 5,188,612 | 2/1993 | Harrington | 604/192 |
| 5,232,454 | 8/1993 | Hollister | 604/192 |
| 5,232,455 | 8/1993 | Hollister | 604/263 X |

*Primary Examiner*—John D. Yasko
*Attorney, Agent, or Firm*—Evan D. Roberts

[57] ABSTRACT

Syringe needle guard assembly provided with a hypodermic needle retaining body having a needle extending therethrough, a needle outlet guard hinged to the body, a needle inlet guard, a needle retaining and guiding structure within the needle outlet guard and a needle inlet guard having a structure positionable over the needle body and the outlet needle guard hinge.

13 Claims, 3 Drawing Sheets

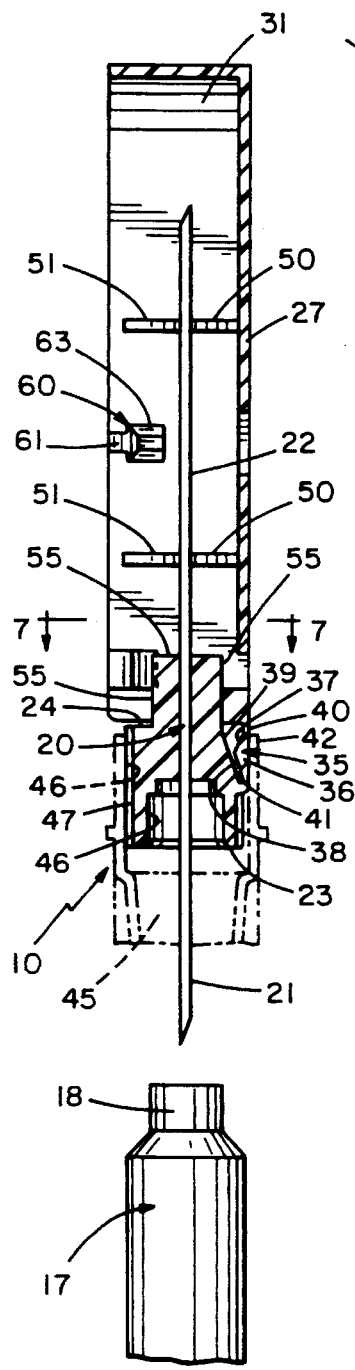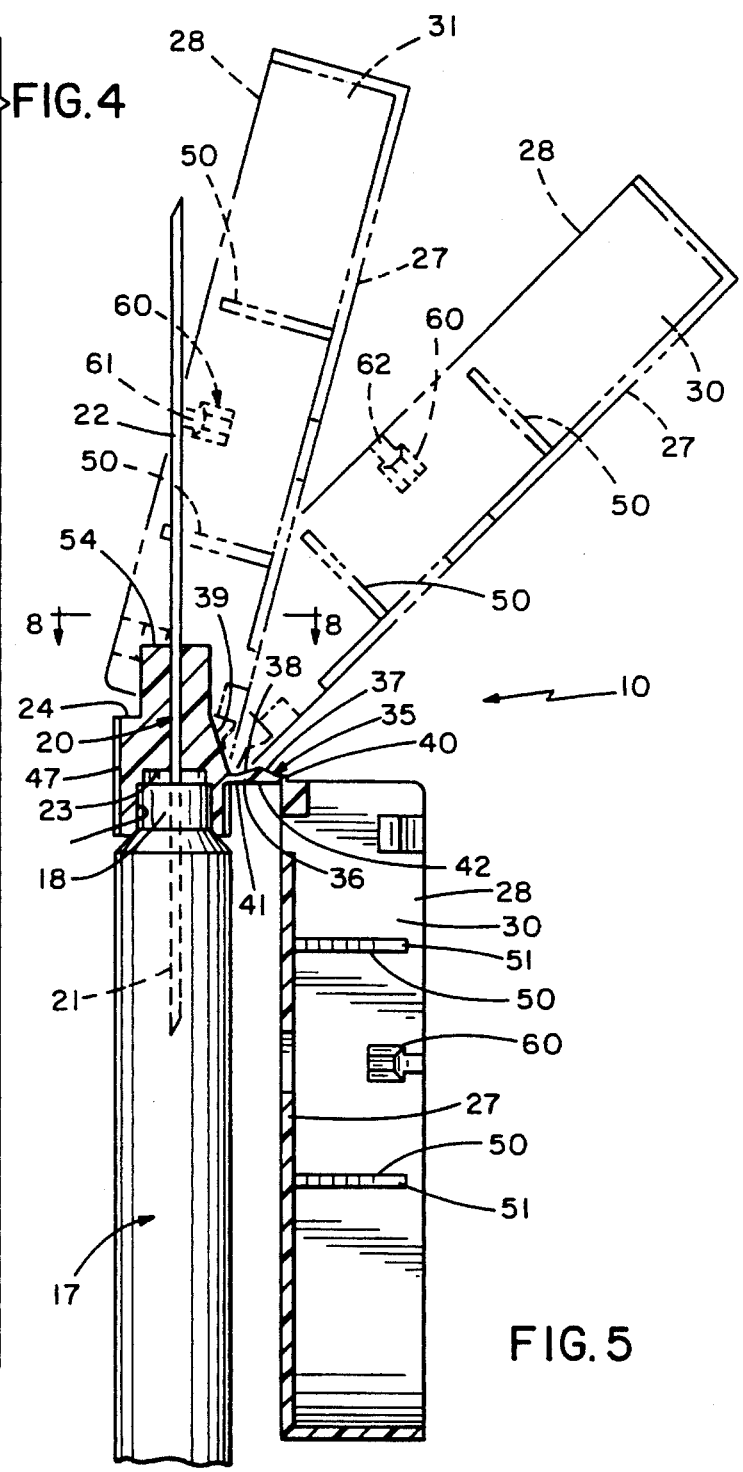
FIG. 4
FIG. 5

SYRINGE NEEDLE GUARD ASSEMBLY

BACKGROUND OF THE INVENTION

Existing known types of syringe needle assemblies often provide a needle guard which is pivotable to and away from the outlet portion of a hypodermic needle of a syringe to protect the needle against unwanted incidental penetration.

The known types of structures typically do not provide protection against the unwanted incidental insertion of an inlet needle portion of a needle extending through a needle body portion when such a structure is utilized with an ampoule-type syringe or a syringe adapted to receive such a needle retaining portion with both an inlet and an outlet requiring protection against unwanted incidental penetration of either the inlet or the outlet portion of the structure.

Also, existing known types of apparatus for syringe needle guard protection do not provide a guard for a needle body inlet portion that cooperates with a needle body outlet guard portion to tend to provide retentive and guarding support for the needle outlet guard portion while protecting both the needle inlet and outlet portions against unwanted incidental penetration.

Some existing known types of syringe needle guard assemblies, although providing outlet needle guard protection of the needle against unwanted incidental insertion of a needle outlet portion, typically have only one structure for either retaining a needle guard assembly over the needle outlet portion, or needle inlet portion, without providing a cooperating needle guard retaining structure for protection of an inlet needle portion and an outlet needle portion to enhance, extend and emphasize the protection that is needed for a needle guard assembly.

Still further, existing known types of syringe needle guard assemblies, although providing a needle guard which is pivotable to and away from the needle outlet portion to protect the outlet portion of the needle from unwanted incidental penetration, they do not provide appropriate structure for guiding the needle laterally into and out of the needle guard while providing a structure for selectively, permanently retaining the needle outlet portion within the needle guard.

Also, existing known types of syringe needle guard assemblies provide a double hinged portion for attaching an outlet needle guard structure, but fail to provide structure for supporting the hinge of the needle outlet guard assembly in a more positive manner while simultaneously protecting the needle inlet and outlet portions to aid in the preclusion of the unwanted incidental removal of the outlet needle guard from guarded position over the needle outlet portion.

SUMMARY OF THE INVENTION

This invention relates to a syringe needle guard assembly for a syringe having an ejection hub adapted to allow fluid to be ejected therethrough from the syringe wherein inlet and outlet portions, if a syringe needle extending through a needle body, are both provided with retaining guards to retain and guard the needle portions against unwanted inadvertent penetration by the needle portions.

More particularly, the structure of this invention provides, among other things, a guard for a needle body inlet portion that cooperates with a needle outlet guard portion to provide retentive and guarding support for a needle outlet guard while protecting both the needle inlet and outlet portions against unwanted, incidental and inadvertent penetration by the needle portions.

In addition, the syringe needle guard assembly of this invention provides structure for guiding the syringe needle laterally into and out of a needle guard while providing for selectively and permanently retaining the needle outlet portion within the needle guard.

Further, this invention provides structure for supporting a double hinged portion of a needle outlet guard in a more positive manner while simultaneously protecting the needle inlet and outlet portions to preclude unwanted incidental removal of the outlet needle guard from guarded position over the needle outlet portion.

Other advantages and novel aspects of the invention hereof will become apparent upon consideration of the following detailed description thereof in conjunction with the accompanying drawings wherein:

FIG. 4 is a side section view of the outlet guard portion of the syringe needle guard assembly showing the inlet guard portion removed and in position to be mounted to the syringe;

FIG. 5 is a side section lateral view of the syringe needle guard assembly showing the needle outlet portion mounted to the syringe and the scope of the pivotal movement of the outlet needle guard relative thereto;

Figure 1:
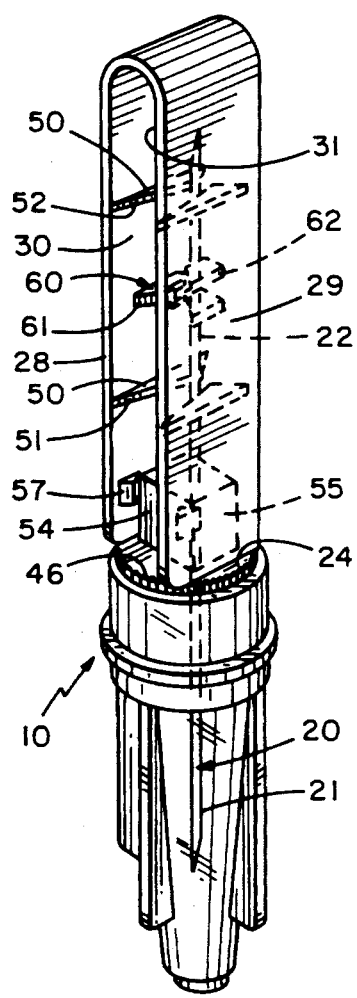
FIG. 1 is an enlarged general perspective view of the syringe needle guard assembly of the invention with the inlet and outlet needle guards in position on the needle body over the syringe needle.

The syringe needle assembly of this invention is generally designated by the numeral 10 (FIGS. 1–5), and generally includes: a hypodermic needle retaining body 11; needle outlet guard 12; and a needle inlet guard 13. Assembly 10 is illustrated herein for use with a syringe 17 having an ejection hub 18 adapted to allow fluid to be ejected therethrough from syringe 17 by a syringe needle 20 positioned through body 11 (FIGS. 1–5 and 10).

Syringe needle 20 has an inlet portion 21 and an outlet portion 22 on respective inlet and outlet side surface ends 23 and 24 of body 11, with said surfaces 23 and 24 connected by cylindrical surface 25. Needle outlet guard assembly 12 has a longitudinally extending bottom enclosure portion 27, and two longitudinal enclosure sides 28 and 29 extending laterally from bottom portion 27 and having respective inner surfaces 30 and 31 forming a cavity in outlet guard 12 to selectively contain needle outlet portion 22.

Figure 2:
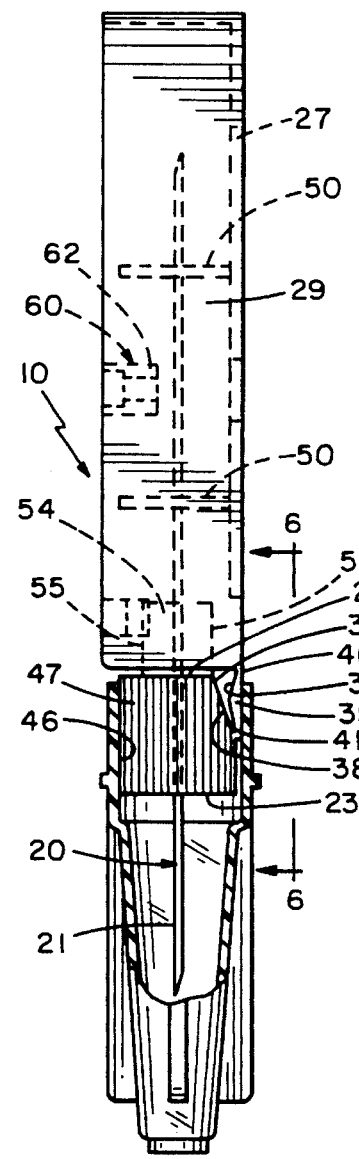
FIG. 2 is a partially sectioned lateral side view of the syringe needle guard assembly showing needle guards in guarding position and the inlet needle guard supporting the outlet needle guard via the outlet guard hinge on the needle body.
Figure 8:
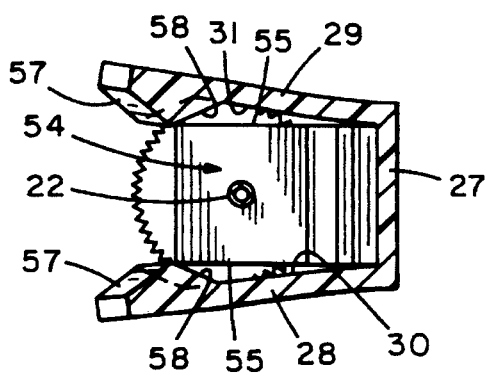
FIG. 8 is a section view taken along line 8—8 of FIG. 5 showing the outlet guard retaining projections deflected away from the body retaining portion as the outlet guard is pivoted thereover.

A hinge portion 35 (FIGS. 2 & 4–6) pivotally secured to, and as an extension of, guard bottom enclosure portion 27 of needle outlet guard 12 is provided with a body 36 having a tapered outer surface portion 37 and an oppositely tapered inner support surface portion 38 (FIGS. 2, 4 & 8).

Inner hinge support surface portion 38 is adapted to be positioned in close complemental proximity with a hinge support surface 39 of body 11. Narrowed pivot portions 40 and 41 on hinge body 36 respectively connect outer needle guard 12 to body portion 11 in an open hinged fashion at narrow hinge pivot portions 40 and 41 (FIG. 5).

An inner cylindrical surface 46 (FIGS. 1–6 & 10) is provided in inlet guard 13 (FIGS. 2–4 & 6) providing an inner surface cavity 45 to contain needle inlet portion 21. Surface 46 is adapted to frictionally receive cylindrical outer surface 47 of needle retaining body 11 and outer surface 42 of hinge 35 of body 11 and outer needle guard 12 (FIGS. 2 & 4). Inlet guard 13 thereby physically retains needle inlet guard 13 over needle inlet portion 21 and hinge 35 to support needle outlet guard portion 12 over needle outlet portion 22.

Multiple entry guides 50 (FIGS. 2–5, 9 & 10) are provided on inner surfaces 30 and 31 of needle outlet guard 12 and have inwardly converging needle entry guiding surfaces 51. A body retaining projection 54, with opposite sides 55 (FIGS. 1–4, 7 & 8) is provided on retaining body 11, normally within outlet guard 12 when guard 12 is in guard position over needle outlet portion (FIGS. 1–8).

Needle guard outlet sides 28 and 29 are laterally flexibly deflectable and are each provided with projections 57 which will similarly flex. Projections 57 have converging tapered surfaces 57 and 58 (FIG. 8) acting in cam action relation with respective sides 55 of body retaining projection 54 (FIG. 8). Flexible sides 28 and 29, by virtue of projections 57, will be deflected laterally by the cam action with sides 55 to allow passage of projection 54 between sides 28 and 29 when said outlet needle guard 12 is pivoted to, and away from, guarding position over outlet needle portion 22 (FIGS. 4 & 5).

When needle outlet guard 12 is in needle guarding position, guard 12 is releasably held in said position by the deflectable flexible incline projections 57 (FIGS. 1–4 & 7). Needle guard 12 is released from the guarding position by pivoting guard 12 about hinge 35 (FIG. 5) whereby flexible sides 28 and 29 and projections 57 will be cammed apart (FIG. 8) by cam action between retaining projection 54 and projections 57 to allow passage of guard sides 30 and 31 past retaining projection 54.

A locking means, generally designated as 60 (FIGS. 1–5, 9 and 10), is provided in needle guard 12 to allow needle guard 12 to be permanently secured in a guard position over outlet needle portion 22 to prevent removal of guard 12 from the guard position over needle portion 22 in guard 12.

Figure 9:
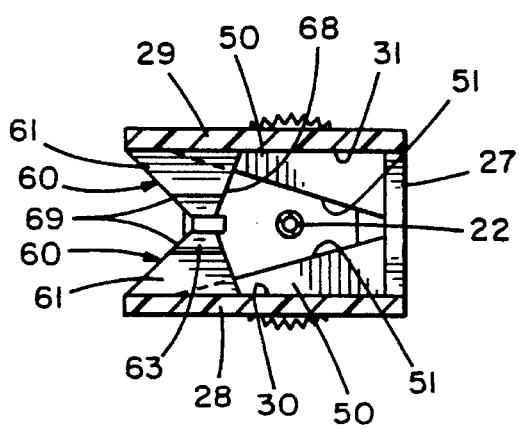
FIG. 9 is a section view taken along line 9—9 of FIG. 3 showing outlet guard internal needle guides.

Locking means 60 includes locking receiving projection 61 extending laterally inwardly into the cavity formed by needle guard side surfaces 30 and 31 of guard 12. A locking entry projection 62 is also provided on inside surface 31 of guard 12 in alignment with locking receiving projection 61 (FIGS. 3 & 10) on opposite surface 30 of guard 12. Projections 61 and 62 are respectively provided with incline surfaces 68 to direct needle outlet portion 12 out of the center of guard 12 as guard 12 is pivotally removed from needle outlet portion 22 (FIGS. 5 & 9).

Figure 3:
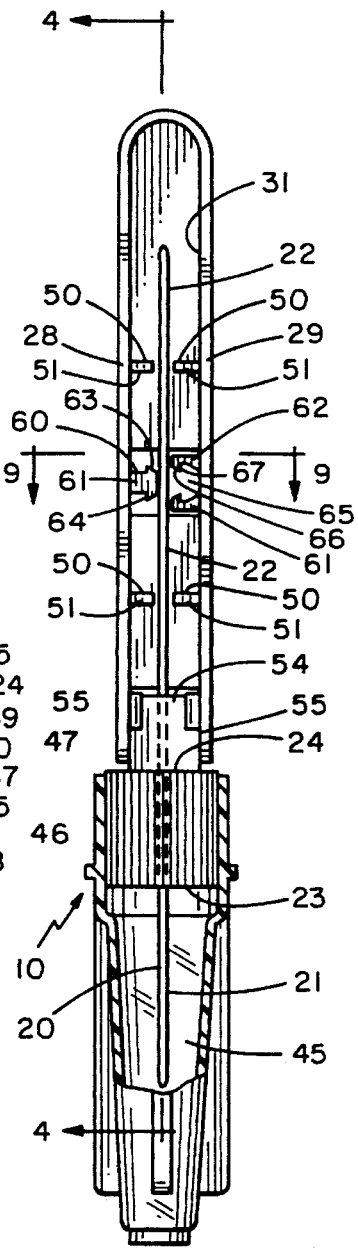
FIG. 3 is a partially sectioned lateral front view of the syringe needle guard assembly showing the needle guards in position.
Figure 6:
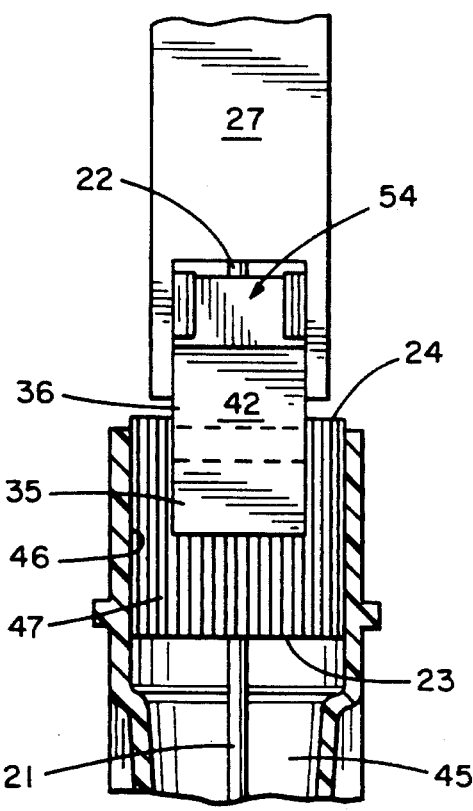
FIG. 6 is a partial view taken along line 6—6 of FIG. 2 showing needle guards in guarding position and the inlet needle guard supporting the outlet needle guard via the outlet guard hinge on the needle body.
Figure 10:
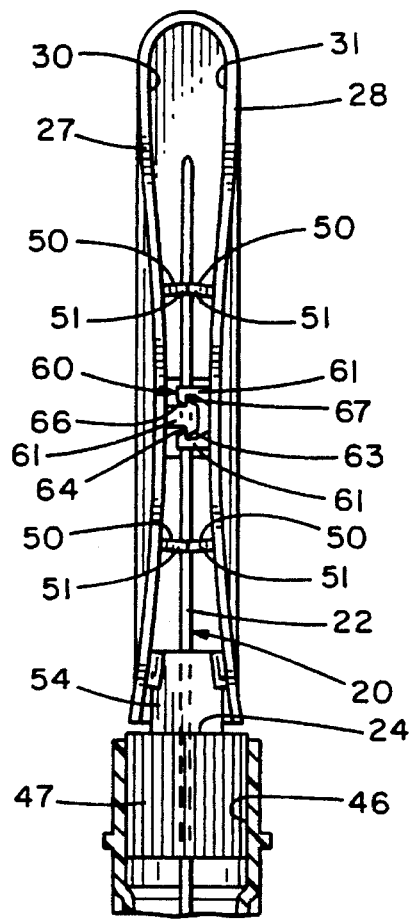
FIG. 10 is a partial front lateral view of the outlet guard portion showing the sides thereof locked together to retain the needle outlet portion therein.

Locking entry projection 61 has an enlarged double tapered tip 63 (FIGS. 3, 4 & 10) which has retaining flange surface 64 (FIGS. 3 & 10) spaced away from surface 30 to which projection 61 is affixed. Locking receiving projection 61 has a retaining cavity 65 (FIG. 3) extending therein laterally to guard side 31 and has a double tapered aperture 66 opening toward other side 30 of the cavity of guard 12 (FIGS. 3 & 10). Cavity 65 has a retaining flange surface 67 spaced away from surface 31 to which projection 62 is affixed.

Locking receiving projection 62 is adapted to frictionally receive locking entry projection 61 (FIGS. 3 & 10) when the flexible sides 28 and 29 of guard 12 are forced towards each other (FIG. 10). Enlarged double tapered tip 63 of locking entry projection will thereby become trapped in cavity 65 of locking receiving projection 61 with locking receiving projection flange surface 64 in engagement with locking entry rejection retaining flange 67 to lock sides 28 and 29 together, trapping outlet needle portion 22 within guard 12.

In operation, syringe needle assembly 10 would be supplied in the form shown (FIGS. 1–3) with needle outlet guard 12 and the needle inlet guard 13 in place on retaining body 11. Needle inlet guard 13 is frictionally mounted on retaining body 11, with needle inlet portion 21 in the cavity 45, and in support of outlet guard hinge 35.

Hinge 35 is double pivotally secured to body 11 at body narrow hinge portion 41 and outer hinge portion 42 to allow 180° pivoting of outlet guard portion 12 away from outlet needle portion 22 in a flexible and loose mode. Therefore, it is important to note that the above described support for hinge 35 is provided to stabilize the flexibly hinged needle outlet guard 12 in position over needle outlet portion 22.

When syringe needle assembly 10 of this invention is ready for use, the user would remove needle inlet guard 13 (FIG. 4) from its position over body 11 and hinge 35. Needle inlet portion 21 is inserted through ejection hub 18 of a syringe or ampoule 17 (FIGS. 4 & 5) with ejection hub 18 frictionally forced into complemental cylindrical surface 46 of retaining body 11, with needle outlet guard 12 mounted onto syringe 17 (FIG. 5).

To expose needle outlet portion 22 for use as a syringe needle, outlet guard is pivoted away from outlet needle portion 22 through an angle of 180° or more (FIG. 5). In the initial pivoting movement of needle guard 12, needle 22 will be guided by incline surfaces 68 of guard 12. As the outlet needle guard 12 is pivoted farther away from outlet needle portion 22, guard 12 is pivoted on body 11 on double hinge pivots 40 and 41 of hinge 35 (FIG. 5).

The loose double hinge configuration of hinge 35 readily allows removal of guard 12 from needle outlet portion 22, and allows guard 12 to be rotated to at least 180° away from the guard position over needle outlet portion 22. This hinge and guard configuration 35 and 12 of the syringe needle assembly 10 of this invention is particularly advantageous to allow the utilization of the syringe needle assembly 10 in small accessible areas such as when used in dentistry.

Figure 7:
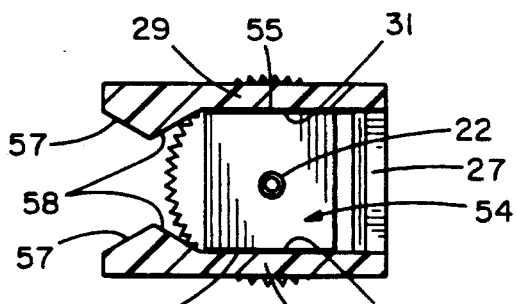
FIG. 7 is a sectional view taken along line 7—7 of FIG. 4 showing a body retaining portion and outlet guard retaining projections in retaining position.

Needle outlet guard 12 is originally firmly held in place over needle outlet portion 22 (FIGS. 1–4) by body retaining projection 54 reacting with tapered surfaces 57 and 58 of respective sides 30 and 31 of needle outlet 12 (FIGS. 5, 7 & 8). In this regard, needle outlet guard 12 is releasably, yet firmly, retained in guard position over outlet needle portion 22 (FIG. 4).

When outlet needle guard 12 is pivoted clockwise away from needle outlet portion 22 (FIG. 5), as described above, respective sides 28 and 29 of guard 12 are first moved apart by the cam action of respective incline surfaces 58 of guard sides 30 and 31 and sides 55 of body retaining projection 54 (FIG. 8) to allow body retaining projection 54 to pass between flexible sides 30 and 31 of guard 12.

After syringe 10 is used, it is desirable to have the guard 12 pivoted counterclockwise to a position over needle outlet 22 (FIGS. 2 & 5). Further, it is desirable to be able to permanently retain needle outlet portion 22 within guard 12 to preclude any accidental, incidental or other unwanted puncturing by needle outlet portion 22.

After use of syringe 10, guard 12 is pivoted counterclockwise from the position shown (FIG. 5) to a position over needle outlet 22 (FIGS. 1–4 & 10) to guard needle outlet 22. During this movement, sides 30 & 31 of guard 12 will be moved outwardly by the cam action between respective sides 55 of body retaining projection 54 and cam surfaces 57 and 58 (FIG. 7) of guard 12 to deflect guard sides 28 and 29 apart to allow body retaining projection 54 to pass therebetween (FIG. 8) to a retaining position as shown (FIG. 7).

After needle outlet portion 22 is once again retained within guard 12 as above described, the flexible sides 28 and 29 of guard 12 are forced toward each other (FIG. 10) to force locking receiving projection 61 of side 30 into locking entry projection 62 by forcing enlarged tapered tip 63 through and beyond tapered aperture 66 of projections 61 and 62 respectively. Conical tip 63 of projection 61 will be trapped in retaining cavity 65 of projection 62 with respective retaining flange surfaces 64 and 67 in complemental engagement against any reverse movement to preclude the removal of locking receiving projection 61 from locking entry projection 62. Thus, needle outlet portion 22 is permanently retained within guide 12 (FIG. 10) to preclude incidental and unwanted re-insertion of needle outlet portion 22.

It is to be understood that the invention is not to be limited to the specific constructions and arrangements shown and described, as it will be understood to those skilled in the art that certain changes may be made without departing from the principles of the inventions.

What is claimed is:

1. A syringe needle guard assembly for a syringe having an ejection hub adapted to allow fluid to be ejected therethrough from the syringe comprising: a hypodermic needle retaining body having an inlet side longitudinally spaced from an outlet side and adapted to be attached to the ejection hub of the syringe to receive fluid therefrom to said inlet side of said body, a hypodermic needle retained longitudinally in and through said body with an inlet portion and an outlet portion respectively extending from said inlet and outlet sides of said body to allow fluid to flow longitudinally therethrough between said body inlet and outlet sides, a needle outlet guard having a longitudinal cavity adapted to receive said needle outlet portion thereinto for guarding said needle, a hinge portion pivotally securing said outlet guard to said body at a lateral side thereof and adjacent said outlet side of said body, to allow said needle outlet guard to pivot to and away from said needle outlet portion for respectively positioning said guard over and away from said needle, said needle outlet guard having means for retaining said outlet guard over said outlet needle portion to guard said needle portion, and a needle inlet guard having an internal cavity adapted to receive said inlet portion of said retaining body and said hinge of said outlet guard thereinto for guarding said inlet needle portion and retaining and positioning said inlet and outlet needle guards on said needle body.

2. A syringe needle guard assembly as defined in claim 1 wherein said needle retaining means includes a body retaining projection extending laterally from said outlet side of said needle retaining body around said outlet needle portion and adapted to move into position between said needle outlet guard sides within the cavity thereof when said outlet guard is pivoted over said needle, and said needle outlet guard sides are provided with a flexible projection on respective sides thereof in the cavity adjacent the pivot end of said outlet needle guard and the opening of the cavity thereof and said body retaining projection and respectively projecting laterally inwardly from said outlet needle guard sides toward each other leaving a normal distance therebetween which is less than the lateral thickness of the body retaining projection extending from said needle retaining body whereby when said outlet needle guard is pivoted over said needle, said side projections will engage said body retaining projection and biasly deflect laterally apart to allow said body projection to move therebetween and beyond and to return to the normal position thereof by the flexible bias of said guard sides to trap said body projection between said needle guard side projections and bottom of said outlet needle guard to tend to retain said needle guard in position on said projection and over said needle for guarding said needle.

3. A syringe needle guard assembly as defined in claim 1 wherein said needle retaining means includes a locking means between said outlet needle guard sides adjacent the opening of the cavity thereof and centrally between the longitudinal ends thereof and includes a locking receiving projection extending inwardly from one inside surface of said outlet needle guard adjacent the opening of the cavity thereof and having a retaining passage extending laterally to said guard and having an aperture toward the other side of the cavity, and a locking entry projection extending inwardly from the other side of the outlet needle guard and adapted to frictionally engage said receiving projection within the aperture thereof for locking said guard sides together across the cavity to preclude the pivoting of said outlet needle guard away from said needle within the cavity.

4. A syringe needle guard assembly as defined in claim 2 wherein said needle retaining means includes a locking means between said outlet needle guard sides adjacent the opening of the cavity thereof and centrally between the longitudinal ends thereof and includes a locking receiving projection extending inwardly from one inside surface of said outlet needle guard adjacent the opening of the cavity thereof and having a retaining passage extending laterally to said guard and having an aperture toward the other side of the cavity, and a locking entry projection extending inwardly from the other side of the outlet needle guard and adapted to frictionally engage said receiving projection within the aperture thereof for locking said guard sides together across the cavity to preclude the pivoting of said outlet needle guard away from said needle within the cavity.

5. A syringe needle guard assembly as defined in claim 3 wherein said locking receiving projection aperture is smaller than the passage thereof, and said locking entry projection has an enlarged end portion adapted to being forced beyond said reduced aperture portion of said locking receiving projection for positive locking of said locking entry projection into said locking receiving projection.

6. A syringe needle guard assembly as defined in claim 5 wherein said locking receiving projection aperture is smaller than the passage thereof, and said locking entry projection has an enlarged end portion adapted to being forced beyond said reduced aperture portion of said locking receiving projection for positive locking of said locking entry projection into said locking receiving projection.

7. A syringe needle guard assembly as defined in claim 4 wherein said locking receiving projection aperture is smaller than the passage thereof, and said locking entry projection has an enlarged end portion adapted to being forced beyond said reduced aperture portion of said locking receiving projection for positive locking of said locking entry projection into said locking receiving projection.

8. A syringe needle guard assembly as defined in claim 1 wherein said hinge comprises a hinge body having a lateral body pivot portion connecting said hinge and body to said needle retaining body, and said hinge having a lateral needle guard pivot portion connecting said hinge body to said needle guard to provide a flexible double pivot hinge whereby said needle guard is pivotable through 180° and away from the guard position over said needle by the length of said hinge body and to an open position 180° away from said needle and longitudinally adjacent the syringe, said needle retaining body has a hinge support surface adjacent said body pivot portion and complemental to said hinge body when said hinge is extended longitudinally parallel to said needle and away from said needle retaining body for supporting and positioning said hinge and needle guard when same are adjacent to each other and said needle inlet guard being adapted to receive said needle retaining body and said hinge thereinto whereby said double flex hinge is retained and positioned adjacent said hinge support surface in guarding position over said outlet portion of said needle.

9. A syringe needle guard assembly as defined in claim 3 wherein said hinge body portion has a gradually enlarged thickness extending from said body pivot generally toward said needle and a gradually diminished thickness extending from a central portion of said hinge body toward said hinge guard pivot, said needle retaining body has a hinge support surface adjacent said body hinge pivot and complemental to said gradually enlarged thickness portion of said hinge when said hinge is extended longitudinally parallel to said needle and away from said needle retaining body for supporting and positioning said hinge and needle guard when same are adjacent to each other, and said needle inlet guard being adapted to receive said needle retaining body and said hinge thereinto whereby said double flexible hinge is retained and positioned adjacent said hinge support surface in guarding position over said outlet portion of said needle.

10. A syringe needle guard assembly as defined in claim 8 wherein said needle retaining means includes a body retaining projection extending laterally from said outlet side of said needle retaining body around said outlet needle portion and adapted to move into position between said needle outlet guard sides within the cavity thereof when said outlet guard is pivoted over said needle, and said needle outlet guard sides are provided with a flexible projection on respective sides thereof in the cavity adjacent the pivot end of said outlet needle guard and the opening of the cavity thereof and said body retaining projection and respectively projecting laterally inwardly from said outlet needle guard sides toward each other leaving a normal distance therebetween which is less than the lateral thickness of the body retaining projection extending from said needle retaining body whereby when said outlet needle guard is pivoted over said needle, said side projections will engage said body retaining projection and biasly deflect laterally apart to allow said body projection to move therebetween and beyond and to return to the normal position thereof by the flexible bias of said guard sides to trap said body projection between said needle guard side projections and bottom of said outlet needle guard to tend to retain said needle guard in position on said projection and over said needle for guarding said needle.

11. A syringe needle guard assembly as defined in claim 9 wherein said needle retaining means includes a body retaining projection extending laterally from said outlet side of said needle retaining body around said outlet needle portion and adapted to move into position between said needle outlet guard sides within the cavity thereof when said outlet guard is pivoted over said needle, and said needle outlet guard sides are provided with a flexible projection on respective sides thereof in the cavity adjacent the pivot end of said outlet needle guard and the opening of the cavity thereof and said body retaining projection and respectively projecting laterally inwardly from said outlet needle guard sides toward each other leaving a normal distance therebetween which is less than the lateral thickness of the body retaining projection extending from said needle retaining body whereby when said outlet needle guard is pivoted over said needle, said side projections will engage said body retaining projection and biasly deflect laterally apart to allow said body projection to move therebetween and beyond and to return to the normal position thereof by the flexible bias of said guard sides to trap said body projection between said needle guard side projections and bottom of said outlet needle guard to tend to retain said needle guard in position on said projection and over said needle for guarding said needle.

12. A syringe needle guard assembly as defined in claim 8 wherein said needle retaining means includes a locking means between said outlet needle guard sides adjacent the opening of the cavity thereof and centrally between the longitudinal ends thereof and includes a locking receiving projection extending inwardly from one inside surface of said outlet needle guard adjacent the opening of the cavity thereof and having a retaining passage extending laterally to said guard and having an aperture toward the other side of the cavity, and a locking entry projection extending inwardly from the other side of the outlet needle guard and adapted to frictionally engage said receiving projection within the aperture thereof for locking said guard sides together across the cavity to preclude the pivoting of said outlet needle guard away from said needle within the cavity.

13. A syringe needle guard assembly as defined in claim 12 wherein said locking receiving projection aperture is smaller than the passage thereof, and said locking entry projection has an enlarged end portion adapted to being forced beyond said reduced aperture portion of said locking receiving projection for positive locking of said locking entry projection into said locking receiving projection.

* * * * *

UNITED STATES PATENT AND TRADEMARK OFFICE
CERTIFICATE OF CORRECTION

PATENT NO. : 5,509,907
DATED : April 23, 1996
INVENTOR(S) : Al Bevilacqua

It is certified that error appears in the above-indentified patent and that said Letters Patent is hereby corrected as shown below:

Claim 9     Line 1     The numeral "3" should be ---8---.

Signed and Sealed this

Twenty-ninth Day of October 1996

Attest:

BRUCE LEHMAN

*Attesting Officer*     *Commissioner of Patents and Trademarks*